(12) United States Patent
Iwasaki (10) Patent No.: US 10,117,791 B2
(45) Date of Patent: Nov. 6, 2018

(54) SANITARY TOWEL

(71) Applicant: DAIO PAPER CORPORATION, Shikokuchuo-shi, Ehime (JP)

(72) Inventor: Ai Iwasaki, Sakura (JP)

(73) Assignee: DAIO PAPER CORPORATION, Ehime (JP)

( * ) Notice: Subject to any disclaimer, the term of this patent is extended or adjusted under 35 U.S.C. 154(b) by 373 days.

(21) Appl. No.: 14/894,251

(22) PCT Filed: May 28, 2014

(86) PCT No.: PCT/JP2014/064129
§ 371 (c)(1),
(2) Date: Nov. 25, 2015

(87) PCT Pub. No.: WO2014/192809
PCT Pub. Date: Dec. 4, 2014

(65) Prior Publication Data
US 2016/0113823 A1 Apr. 28, 2016

(30) Foreign Application Priority Data
May 28, 2013 (JP) .................................. 2013-111645

(51) Int. Cl.
A61F 13/15 (2006.01)
A61F 13/475 (2006.01)
A61F 13/47 (2006.01)
A61F 13/45 (2006.01)

(52) U.S. Cl.
CPC ...... *A61F 13/4758* (2013.01); *A61F 13/4704* (2013.01); *A61F 13/4753* (2013.01); *A61F 2013/4512* (2013.01); *A61F 2013/4708* (2013.01)

(58) Field of Classification Search
CPC .............. A61F 13/4758; A61F 13/4704; A61F 13/4753; A61F 2013/4708; A61F 2013/4512
USPC ........................................ 604/385.24, 385.28
See application file for complete search history.

(56) References Cited

U.S. PATENT DOCUMENTS

| | | | |
|---|---|---|---|
| 7,163,530 | B1 | 1/2007 | Toyoshima et al. |
| 2001/0023343 | A1 | 9/2001 | Mizutani et al. |
| 2004/0260264 | A1 | 12/2004 | Otsubo |

(Continued)

FOREIGN PATENT DOCUMENTS

| | | |
|---|---|---|
| JP | 2001-137282 | 5/2001 |
| JP | 2003-180739 | 7/2003 |
| JP | 2004-290498 | 10/2004 |

(Continued)

*Primary Examiner* — Jacqueline Stephens
(74) *Attorney, Agent, or Firm* — Norris McLaughlin, P.A.

(57) ABSTRACT

In a sanitary towel an inside elastic member is disposed in an intermediate portion in a width direction corresponding to a non-joint area of an upper layer side cuff surface, and when standing-up toward a skin side with an inside edge portion of a joint area as a base in a standing state, a portion between from the inside elastic member to an inside edge portion of a joint area works as a standing wall and a portion outside the inside elastic member works as a skin-abutting surface when the sanitary towel is worn, and a portion that works as a skin-abutting surface is further outward in a towel width direction in the standing state than in the folded state.

6 Claims, 5 Drawing Sheets

(56) References Cited

U.S. PATENT DOCUMENTS

2009/0054862 A1* 2/2009 Tatsukawa .......... A61F 13/4942
604/365
2015/0080830 A1 3/2015 Miura

FOREIGN PATENT DOCUMENTS

| JP | 2005-13268 | 1/2005 |
| JP | 2005-523139 | 8/2005 |
| JP | 3847046 | 9/2006 |
| JP | 2008-246093 | 10/2008 |
| JP | 2011-120764 | 6/2011 |

* cited by examiner

SANITARY TOWEL

BACKGROUND OF THE INVENTION

The present invention relates to a sanitary towel, also known as a sanitary napkin, that mainly absorbs menstrual blood, vaginal discharge or the like, especially a thin sanitary towel provided with solid gathers each standing on a at both sides of a skin-facing front of the sanitary towel.

In this kind of sanitary towel, due to requirements of, in addition to being free from an uncomfortable feeling, being excellent in mountability, being transportable, being excellent in packaging properties, and being efficient in logistics and cost saving, an effort to make the sanitary towel thin and compact has progressed. However, in such a thin sanitary towel, in order not to damage mountability, generally, solid gathers are not provided. Therefore, there tends to occur a gap between the towel and the skin, and lateral leakage of menstrual blood and body liquid such as urine is likely to occur.

As the solid gather, various forms have been developed, and there are many technical literatures relating to this. For example, JP 2004-230498 A, a solid gather is disclosed in which, when a side nonwoven fabric is disposed in the intermediate portion in a height direction with a plurality of elastic expandable members, adhered to an absorber side in a state in which front and back end portions are laminated by folding in a Z shape in a cross-section, the solid gather stands-up on a front side while forming a pocket with an opening directed to an inside in an L-shaped cross section with a site where the elastic expandable members are disposed as a bending point. Further, similarly in JP 2004-290498 A, a solid gather that stands-up simply in line by adhering to the absorber side in a state where front and back end portions of the side nonwoven fabric are folded back outward is disclosed.

Further, in the following JP 3847046, an absorbing article is disclosed in which an elastic material that is disposed along a free end and exhibits an elastic contractile force and an elastic material that forms a contract action line approaching from a base end side to a free end side as goes from both end sides in a vertical direction of the leakage blocking side wall to an intermediate position in a vertical direction are disposed, and both end portions in the vertical direction of the leakage blocking side wall are joined to a liquid receiving side surface of which free ends are directed to the outside in a width direction.

Further, in the following JP 2011-120764 A, a sanitary towel in which a leakage-blocking wall is joined to a front sheet along a longitudinal direction above an absorber and includes a standing portion that stands up during use with the joint portion as a base point and a body side covering portion that extends externally in a width direction from the joint portion and covers a side surface portion of an absorptive body is disclosed.

SUMMARY OF THE INVENTION

As a solid gather that is used in commercially available sanitary towels, the solid gather that has an L-shaped cross section or a linear cross section, which are described in JP 2004-290498 A, are usual. However, since the sanitary towel with the L-shaped cross section has to be laminated by folding a side nonwoven fabric in a Z-shaped cross section, there were problems of greater than desired thickness and an uncomfortable feeling occurring during wearing. Further, in a linear solid gather obtained by externally folding back the side nonwoven fabric only once, a standing height is insufficient and a gap tends to occur between the sanitary towel and the skin, and further, a standing wall portion for blocking the body liquid from flowing sideward was difficult to form.

Further, as described in JP 3847046, in the case of the solid gather in which a width of a skin abutting surface in which an elastic material is disposed in a bending manner along a solid gather longitudinal direction changes, and in the case of a solid gather that stands up in a T-shaped cross section as described in JP 2011-120764 A, there was wearing comfort is degraded and the sanitary towel is not as thin as desired.

Still further, while a sanitary towel that has a certain degree of absorber thickness like a conventional sanitary towel has a structure that can absorb and hold the body liquid in a wide range of the absorber by diffusing in the inside of the absorber after the body liquid is absorbed by the absorber, in the case of a thin sanitary towel, since a high water-absorbing resin is contained at a high density in the absorber, a ratio of the body liquid that diffuses into the inside of the absorber is low, and after the body liquid diffuses over a surface of the sanitary towel, the body liquid is absorbed and held by the absorber. Therefore, in the case of the thin sanitary towel in particular, since it is important to secure a surface portion effective for absorbing the body liquid over a wide range, it is necessary to avoid a situation in which the solid gather falls down toward the inside during wearing to narrow a surface width effective for absorbing the body liquid. In this point, in the case of the solid gather having the L-shaped cross section described in JP 2004-290498 A, the solid gather described in JP 3847046, in which a width of the skin-abutting surface portion of the standing-up proximal end becomes narrower in a groin portion, and the solid gather having the T-shaped cross section described in JP 2011-120764 A, there was a fear that, due to pressure from the inside portion of a base of the leg and movement of the leg, the skin-abutting portion of the standing-up proximal end of the solid gather tends to fall down to the inside and there is a fear that the surface width effective for absorbing the body liquid may be narrower.

In this connection, a main item of the present invention is to provide a sanitary towel provided with a solid gather and which, even when the sanitary towel is thin, is free from an uncomfortable feeling during wearing and is high in a body liquid blocking effect, and in which falling down of the solid gather to the inside during wearing does not occur.

As the present invention according to aspect one, for solving the above-described problems, a sanitary towel in which an absorber is disposed at least on a front side of an impervious back sheet and a solid gather is formed along a longitudinal direction of each side portion of the front (skin-facing) side is characterized in that:

the solid gather is, in a folded state, provided with a non-joint area that is not joined to a constituent member on a lower layer side in a longitudinal direction range containing at least a body liquid discharging portion of double sheets folded back on a center side in a width direction and in the proximity portion of a cuff portion, and, an elastic member is disposed along a longitudinal direction on the sheet on an upper layer side of an intermediate portion in a width direction corresponding to the non-joint area;

both the double sheets are formed to an end edge of the sanitary towel with a position further toward the end edge of the sanitary towel than the end edge of the non-joint area as a base with respect to the sanitary towel longitudinal direction, and are joined in an upper layer side joint area formed with a narrower width than a sheet width on an upper side with respect to the sanitary towel width direction; and the solid gather is configured such that, by standing up on a skin side with an outside edge portion of the non-joint area as a base in a standing state, the solid gather acts as a standing wall in which a portion between from the elastic member to the outside edge portion of the non-joint area protrudes from a front side of the absorber, and the outside portion from the elastic member acts as a skin-abutting surface when the sanitary towel is worn, and a portion that works as the skin-abutting surface moves further toward the outside in the sanitary towel width direction in the standing state of the gather than in the folded state of the gather.

According to aspect one of the present invention, firstly, in a folded state of the solid gather before wearing, a structure is provided, in which a double sheet structure folded back on a center side in the width direction is formed, a non-joint area that is not joined to the constituent member (the absorber, the impervious back sheet and the like) on a lower layer side in the longitudinal direction range including at least the body liquid discharging portion and in the proximity portion of the cuff portion of the double sheets is provided, and the elastic member is disposed along the longitudinal direction in an intermediate portion in the width direction corresponding to the non-joint area. Further, the double sheets are formed to the end edge of the sanitary towel with a position further toward the end portion of the sanitary towel than the end edge of the non-joint area as a base with respect to the sanitary towel longitudinal direction, and are joined in an upper side joint area formed with a narrower width than a sheet width on the upper layer side with respect to the sanitary towel width direction.

In a state where the solid gather is raised when wearing such a sanitary towel, when the solid gather stands up on the skin side with the outside edge portion of the non-joint area as a base, a portion between from the elastic member to the outside edge portion of the non-joint area acts as a standing wall that protrudes from a surface side of the absorber when the cuff state is released and an outside portion from the inside elastic member acts as the skin abutting surface when the sanitary towel is worn. Here, since the elastic member is disposed in the intermediate portion in the width direction corresponding to the non-joint area, when raised with the outside edge portion of the non-joint area as the base by the contraction of the elastic member, the elastic member is pulled in the outside edge portion direction of the non-joint area, and a portion that acts as the skin-abutting surface is configured such that the standing-up state moves further outward in the sanitary towel width direction than the folded state.

Therefore, when wearing the sanitary towel, the risk of the skin-abutting surface of the solid gather falling down toward the inside is largely reduced, a wide surface width of the absorber effective for absorbing the body liquid is secured, and even with the thin sanitary towel, high absorbance is secured. Further, since a cross sectional shape of the solid gather forms a standing wall in which, with the inside elastic member as a bending point, an absorber side from the bending point protrudes from a surface side of the absorber, blocking of the body liquid is secured by the standing wall, and the lateral leakage is blocked. Further, since an outside extended stock extended further outward than a side edge of the absorber is disposed on a cuff surface on an upper side of the solid gather and, the skin-abutting surface is configured to move further outward in the sanitary towel width direction in a standing state than in the folded state, the skin-abutting surface of the solid gather runs off outside of the side edge of a panty so that the sanitary towel is easily worn with the panty, and a risk that the solid gather falls down on the inside by the pressure from the inside of a root portion of the leg or the movement of the leg is largely reduced. Further, since the solid gather is formed from a sheet of a two-layer structure including a lower layer side cuff surface and an upper layer side cuff surface in a folded state, the solid gather thinner and wearing comfort is greater.

Further, an angle by which the skin-abutting surface contacts the skin is adjusted or wearing comfort is increased by forming the upper layer joint area in which the double sheets are joined to each other in a predetermined region. Specifically, the double sheets are formed up to a towel end edge with a position more toward the towel end portion than an end edge of the non-joint area as a base with respect to as towel longitudinal direction and are joined in the upper layer side joint area formed with a narrower width than a sheet width on the upper layer side with respect to a towel width direction. By disposing the base in the towel longitudinal direction of the upper layer side joint area at a position further toward the end portion than the end edge of the non-joint area, since a tip end (free end) of a portion that works as the skin-abutting surface on the upper layer side tends to incline toward the skin side and the skin-abutting surface tends to fit along the skin, the solid gather may be prevented from falling down on the inside of the solid gather. Further, when a joint area that may cause wearing discomfort is formed into a small area by forming the width in the towel width direction of the upper layer side joint area with a narrower width than the sheet width of the upper layer side, wearing comfort is increased.

As a present invention according to aspect two, a sanitary towel in which an absorber is disposed at least on a surface side of an impervious back sheet and a solid gather is formed along a longitudinal direction of each of front both sides is characterized in that:

when the solid gather is folded back in a folded state to a lateral side at a folding back portion disposed at a position where a sheet extended in a center side direction from a lateral side of the sanitary towel overlaps the absorber, a lower layer side joint area that has a lower layer side cuff surface and an upper layer side cuff surface and in which the lower layer side cuff surface and a constituent member on a lower layer side of the lower layer side cuff surface are joined is formed over a predetermined area in a center side direction from the lateral side of the sanitary towel, a non-joint area that is in a longitudinal direction range including at least a body liquid discharging portion and in which the lower layer side cuff surface and the constituent member on a lower layer side are joined in the vicinity portion of the cuff portion is formed, an upper layer side joint area in which the upper layer side cuff surface and the lower layer side cuff surface are joined in the both end portions in the sanitary towel longitudinal direction is formed, an outside extended stock in which the outside in the width direction of the upper layer side cuff surface is extended further outside than an end edge of the absorber is disposed on the upper layer side cuff surface, an inside elastic member is disposed along the longitudinal direction in an intermediate portion in a width direction corresponding to the non-joint area, of the upper layer side cuff surface, and further outside in the width direction, an outside elastic member is disposed along the longitudinal direction, the upper layer side joint area is formed to the end edge or the sanitary towel with a position further toward an end portion of the sanitary towel than the end edge of the non-joint area as a base relative to the sanitary towel longitudinal direction, and is formed with a narrower width than a width of the upper layer side cuff surface with respect to the sanitary towel width direction, and the solid gather, by standing up on a skin side with an inside edge portion of the lower layer side joint area as a base in a standing state, acts as a standing wall from which a portion from the inside elastic member to the inside edge portion of the lower layer side joint area protrudes from a front side of the absorber, and an outside portion of the inside elastic member acts as an abutting surface at the time of wearing, and a portion that works as the abutting surface is configured to move more to the outside in the sanitary towel width direction in the standing state than in the folded state. The present invention defines the structure of a solid gather more specifically.

As the present invention according to aspect three, there is provided the sanitary towel according to any one of aspect one and two in which a thickness of a portion excluding a central elevated portion, i.e., the absorber portion, is set to 3 mm or less when the central elevated portion, i.e., the absorber, is formed in a portion corresponding to the body liquid discharging portion of the wearer.

In the invention according to the third aspect, as the thin sanitary towel, a thickness is set to 3 mm or less (a thickness of a portion excluding the central elevated portions when the central elevated portion, i.e., the absorber portion, is formed in a portion corresponding to the body liquid discharging portion) of the wearer.

As the present invention according to the fourth aspect, the sanitary towel according to any one of aspects one to three is provided, in which, in the standing state of the solid gather, the skin-abutting surface is formed such that the width of the portion extending outward of the side edge of the absorber is larger than the width of a portion that intervenes in a position that overlaps with the absorber.

According to the present invention of aspect four, in the standing state of the solid gather, as a degree to which the abutting-surface is extended outward of the side edge of the absorber, when the width of a portion that extends outward is formed larger than the width of a portion that intervenes in the position overlapping with the absorber, the skin-abutting surface is prevented from falling down on the inside.

As the present invention according to aspect five, the sanitary towel according to any one of aspects two to four in which the outside elastic member is disposed in an intermediate portion in the width direction of the outside extended stock portion of the upper layer side cuff surface is provided.

In the invention according to aspect five, a disposition position of the outside elastic member is defined. The outside elastic member is preferably disposed in an intermediate portion in the width direction of the outside extended stock portion of the upper layer side cuff surface. By this, the elastic member is disposed over a wide range of the skin-abutting surface and a contact surface with the skin increases to be able to block the leakage.

As the present invention according to aspect six, the sanitary towel according to any one of aspect two to five in which the tension of the outside elastic member is set equal to or larger than the tension of the inside elastic member is provided.

In the invention according to aspect six, by setting the tension of the outside elastic member equal to or larger than the tension of the inside elastic member, the skin-abutting surface of the solid gather tends to stand in a cross-sectional shape inclined toward the inside, and the conformation to the skin is further improved.

As the present invention according to aspect seven, the sanitary towel according to aspect two to six in which the lower layer side joint area is formed from the lateral side of the sanitary towel up to the position that overlaps with the absorber is provided.

In the invention according to aspect seven, when a range of the joint area that joins the lower layer side cuff surface to the lower layer side constituent member is formed from a lateral side of the sanitary towel up to a position that overlaps with the absorber, a standing wall of the solid gather that stands up with the inside edge portion of the joint area as a base is formed in the intervening position of the absorber, whereby the body liquid that is blocked by the standing wall is made readily absorbable.

As detailed in the above, according to the present invention, even in the thin sanitary towel, the sanitary towel provided with the solid gather that is free from the uncomfortable feeling when wearing, is high in the body liquid blocking effect, and can block the falling on the inside when wearing is provided.

DETAILED DESCRIPTION OF THE INVENTION

Hereinafter, embodiments of the present invention will be detailed with reference to the drawings.

Fundamental Configuration of Sanitary Towel 1

Figure 1:
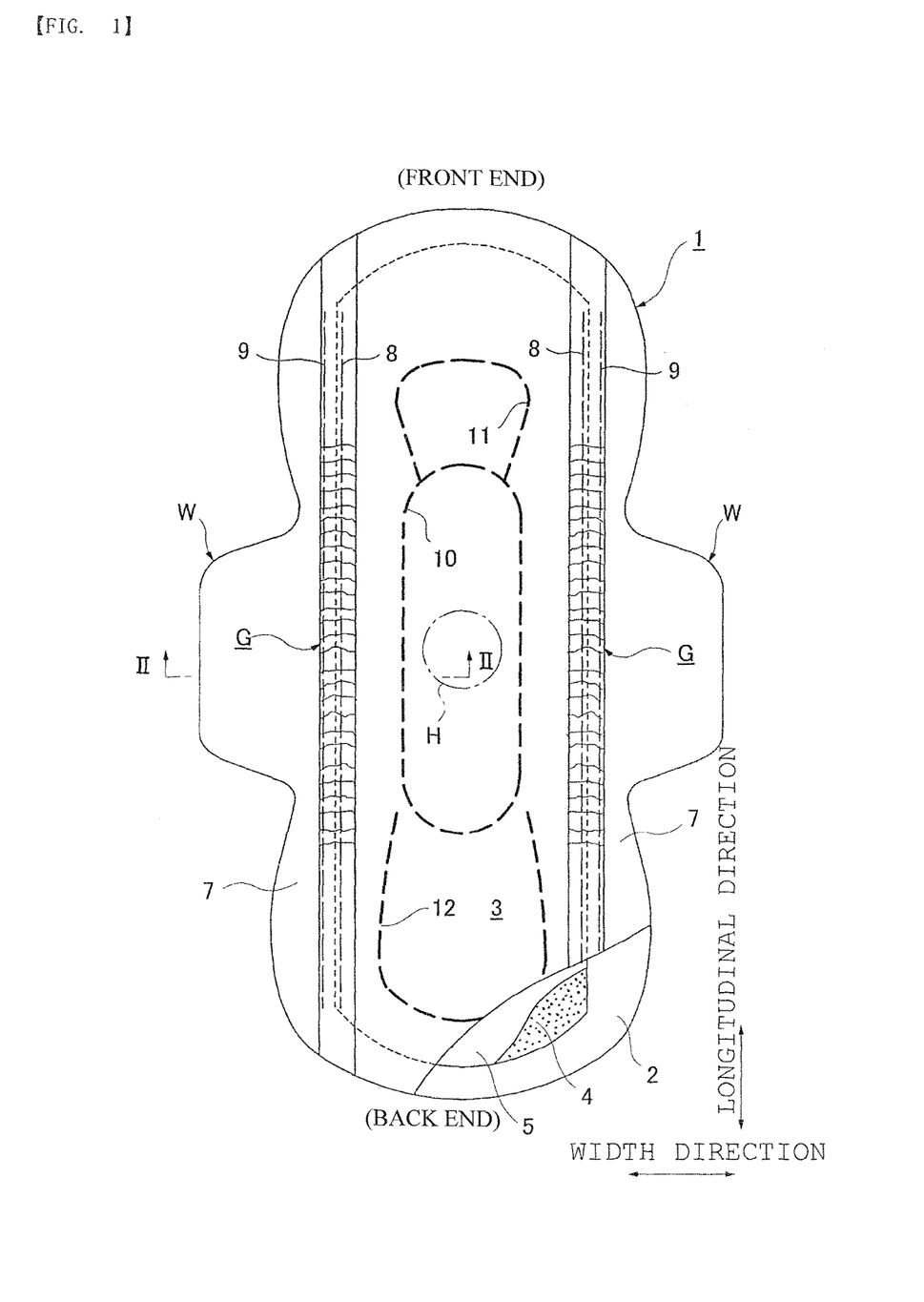
FIG. 1 is a partially broken development view of a sanitary towel 1 according to the present invention.
Figure 2:
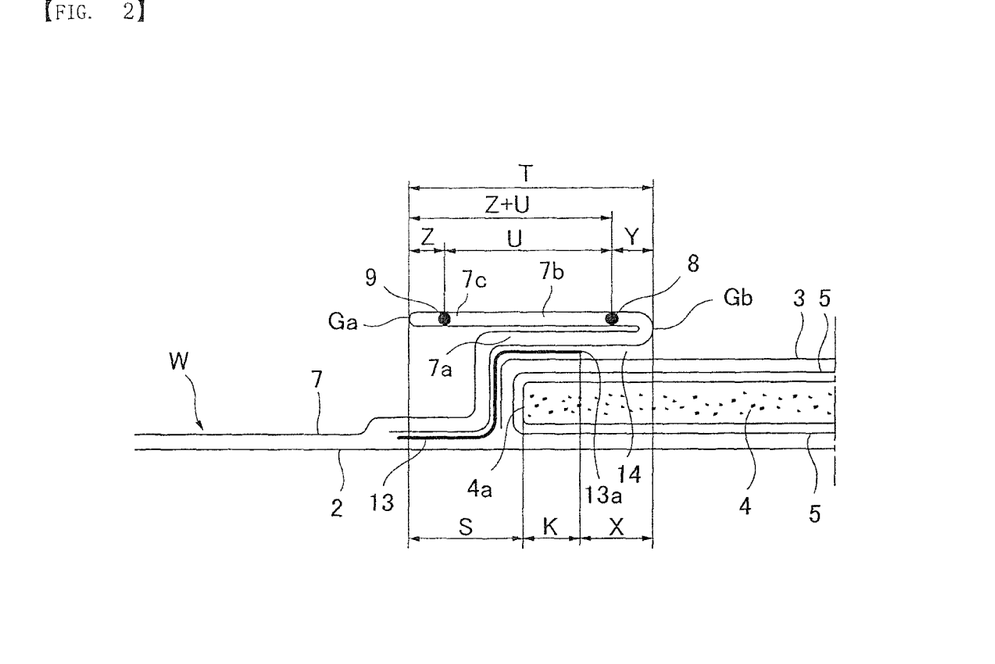
FIG. 2 is a cross-sectional view illustrating a folded state of a solid gather G (II-II line arrow view of FIG. 1).

A sanitary towel 1 according to the present invention includes, as illustrated in FIG. 1 and FIG. 2, an impervious back sheet 2 made of a polyethylene sheet, a polypropylene sheet, or the like, a pervious front sheet 3 that speedily transmits menstrual blood, vaginal discharge, or the like, an absorber 4 that is interposed between the both sheets 2 and 3 and made of fluffy pulp, synthetic pulp, or the like, a crepe paper 5 surrounding the absorber 4 for holding a shape and improving the diffusivity of the absorber 4, and side nonwoven fabrics 7 and 7 each disposed along a longitudinal direction at a respective side of the sanitary towel 1. In the circumference of the absorber 4, at upper and lower end edge portions, outer peripheries of the impervious back sheet 2 and the pervious front sheet 3 are joined by an adhesive such as hot melt or the like or a joining means such as heat seal, or the like, and at both side edge portions, the impervious back sheet 2 extended further sideward than the absorber 4 and the side nonwoven fabric 7 are joined by an adhesive such as hot melt or the like or a joining means such as heat seal, or the like, and wing-like flaps W and W protruding sideward are formed from a composite sheet portion made of the impervious back sheet 2 and the side nonwoven fabric 7.

The sanitary towel 1 according to the present invention is preferably made into a thin towel of which thickness is set to 3 mm or less except for a central elevated portion of the absorber (not shown) which is a portion corresponding to an area circumscribing an area of the wearer including a body liquid discharging portion of the wearer. Further, a towel for daytime use having a total length in the longitudinal direction of 20 to 30 cm is especially of interest in embodiments of the invention because the towel of the invention is able to respond to the movement of legs when a wearer is walking in the daytime or the like.

Hereinafter, a structure of the sanitary towel 1 will be further detailed.

As the impervious back sheet 2, sheet materials having at least the water shieldability such as sheets of olefinic resin such as polyethylene, polypropylene or the like are used. However, other than these, the impervious back sheet may be a laminated nonwoven fabric obtained by laminating the nonwoven fabric on a polyethylene sheet or the like, or a nonwoven fabric sheet in which the imperviousness is substantially secured by providing a waterproof film on the fabric and the like can be used. In recent years, water shielding materials having moisture permeability tend to be used from the viewpoint of mitigating dampness. The water shieldable and moisture permeable sheet material is a microporous sheet obtained by monoaxially or biaxially stretching after molding a sheet by melt kneading an inorganic filler in the olefinic resin such as polyethylene, polypropylene or the like.

Then, as the pervious front (i.e., wearer-facing) sheet 3, a porous or nonporous nonwoven fabric is preferably used. As a raw material fiber that constitutes the nonwoven fabric, other than synthetic fibers such as olefins such as polyethylene, polypropylene or the like, polyesters, polyamides, or the like, recycled fiber such as rayon, cupra, or the like, and natural fiber such as cotton or the like may be used, and the nonwoven fabric obtained according to an appropriate processing method such as the spunlace method, the spunbond method, the thermal bond method, the melt-blown method, the needle punch method or the like may be used. Among these processing methods, the spunlace method is excellent in flexibility of nonwoven fabric produced, the spunbond method is excellent in producing nonwoven fabric of superior drape, and nonwoven produced by the thermal bond method and by the melt blowing method are excellent in being bulky and soft.

When the center-high portion of the absorber is formed in the groin region, an oblong embossing 10 is formed on a surface of the pervious front sheet 3 to hold the elevated central portion at a predetermined position and so that the elevated central portion protrudes predominantly on the front side of the sanitary towel 1, to confine the absorbed body liquid and the like. Further, in a front side region, a substantially inverse U-shaped embossing 11 extends to the wearer's groin region, and, toward the back end of the towel 1, a substantially U-shaped embossing extends to directly behind the groin region.

Although including the pervious front sheet 3 is preferable, it is possible not to include the previous front sheet 3 in order to make the towel thinner. When pervious front sheet 3 is not used, it is preferable to use crepe paper 5 or a nonwoven fabric to surround the absorber 4 or to cover only a front side of the absorber 4.

As the absorber 4 that is interposed between the impervious back sheet 2 and front sheet 3, one obtained by mixing a superabsorber resin in a pulp, or one obtained by mixing chemical fibers in the pulp and by further mixing the superabsorber resin is used. The absorber 4 is, as illustrated in the drawing, desirably surrounded by crepe paper 5 for maintaining a shape, speedily diffusing the menstrual blood or the like, and blocking the once absorbed menstrual blood or the like from turning back. As the pulp referred to above, cellulose fibers such as chemical pulp, molten pulp or the like obtained from wood, or artificial cellulose fibers such as rayon, acetate or the like may be used, and softwood pulp being preferred over hardwood pulp from the viewpoint of function and cost.

Further, the absorber 4 may be mixed with the synthetic fibers. As the synthetic fibers, for example, polyoelefins such as polyethylene, polypropylene, or the like, polyesters such as polyethylene terephthalate, polybutylene terephthadate, or the like, polyamides such as nylon, or the like, and copolymers thereof may be used, and two kinds thereof may be mixed and used. Further, also a sheath/core fiber with a high-melting point fiber as a core and a low-melting point fiber as a sheath, a side-by-side fiber, and a composite fiber such as divided fiber may be used. When the synthetic fiber is a hydrophobic fiber, it is desirable that the fiber surface be treated with a hydrophilizing agent for imparting affinity to the body liquid.

As the superabsorber resin, what is obtained by partially crosslinking water-swelling polymers such as polyacrylate crosslinked products, self-crosslinked polyacrylates, saponified products of acrylic acid ester-vinyl acetate copolymer crosslinked products, crosslinked products of isobutylene-maleic anhydride copolymers, polysulfonate crosslinked products, polyethylene oxide, polyacrylamide or the like are suitable. Among these, acrylic acid or acrylate polymers excellent in an amount of water absorption and water absorption rate are preferable. In the superabsorber resin having the water absorption performance described above, in the production process, the water absorption power and the water absorption rate can be controlled by adjusting the crosslinking density and the crosslinking density gradient. A content of the superabsorber resin is desirable to be set to 10 to 60% of a weight of the absorber. When the content of the superabsorber resin is less than 10%, sufficient absorbing power cannot be imparted, and when the content exceeds 60%, there is no entanglement between pulp fibers, and the sheet strength is degraded and breaks or cracks tend to occur.

As in the present embodiment, when the crepe paper 5 surrounding the absorber 4 is used, resultantly, the crepe paper 5 is interposed between the pervious front sheet 3 and the absorber 4, and the body liquid is rapidly diffused by the crepe paper 5 excellent in absorbability, and, at the same time, the menstrual blood or the like is blocked from turning back. Incidentally, in order to make the towel thinner, the crepe paper 5 may not be used or may be used so as to cover only the front side not by surrounding.

As the side nonwoven fabric 7 described above, a water-repellent-finish nonwoven fabric or a hydrophilic nonwoven fabric can be used from a viewpoint of the function to which importance is attached. For example, if functions, such as blocking menstrual blood, a vaginal discharge, or the like from permeating, or touching the skin, are thought as important, it will be desirable to use the water-repellent-finish nonwoven fabric which is coated with a silicone, paraffin, alkyl chromic chloride water repellent, or the like. If the absorptivity of the menstrual blood or the like in the wing-like flaps W and W described above is thought as important, it is desirable to use synthetic fiber of polymers comprising a hydrophilic group, for example, an oxidation product of a polyethylene glycol, or the like, or a synthetic fiber which has been made to swell or become porous by being treated with a metal salt such as a stannic chloride, the surface of the fiber partially dissolving to render the surface porous and the fiber swelling and becoming further porous by precipitating hydroxide of the metal in the fiber, or a hydrophilic nonwoven fabric to which hydrophilicity has been imparted by capillary action. It is preferable to use nonwoven fabric manufactured by SMMS (spun-melt-melt-spun), air through, and so on as a raw material. The basis weight is preferably about 30 to 45 $g/m^2$.

In the inward side of the side nonwoven fabric 7, as illustrated in FIG. 2, the side nonwoven fabric 7 is folded back in substantially two, in the inside of the double sheets, one or a plurality of, in the illustrated example, two of the inside elastic member 8 and the outside elastic member 9 in which both ends or an appropriate position in the longitudinal direction are fixed at an intermediate portions in a height direction are disposed, and the solid gathers G and G in which the double sheet portion is erected on a front side by its contractile force are formed. The structure of the solid gather G will be more specifically described below.

Structure of Solid Gather G

When the solid gather G is, in a folded state, as illustrated in FIG. 2, folded back on a lateral side at a cuff portion Gb disposed at a position where the side nonwoven fabric 7 extended in a central side direction from a lateral side of the towel, a lower layer side joint area 13 that has a lower layer side cuff surface 7a and an upper layer side cuff surface 7b and in which the lower layer side cuff surface 7a and a constituent member on the further lower layer side (the pervious front sheet 3, the impervious back sheet 2 or the like) are joined over a predetermined region in a direction from a lateral side to the center side of the towel is formed, a non-joint area 14 in which the lower layer side cuff surface 7a and the constituent member on the lower layer side are not joined in the longitudinal direction range including at least the body liquid discharging portion H and in the vicinity of the cuff portion Gb is formed, and an upper layer side joint area 15 (see FIG. 5) in which the upper layer side cuff surface 7b and the lower layer side cuff surface 7a are joined at both ends in the towel longitudinal direction is formed, on the upper layer side cuff surface 7b, an outside extended stock 7c in which the outside in the width direction of the upper layer side cuff surface 7b is extended outward of the side edge 4a of the absorber 4 on the upper layer side cuff portion 7b is disposed, the inside elastic member 8 is disposed along the longitudinal direction at an intermediate portion in a width direction corresponding to the non-joint area 14 of the upper layer side cuff surface 7b, and on more outside than this in the width direction, preferably the outside elastic member 9 is disposed along the longitudinal direction in the intermediate portion in the width direction of the outside extended stock 7c portion.

That is, as illustrated in FIG. 2, in the side nonwoven fabric 7, a portion from a lateral side to a position of distance K inward of the side edge 4a of the absorber 4 of the lower layer side cuff surface 7a is joined to the constituent member on the lower layer side by the lower layer side joint area 13 in the longitudinal direction range including at least the body liquid discharging portion H, a portion from the inside edge portion 13a of the lower layer side joint area 13 to a position of distance X inward is made a non-joint area 14, the cuff portion Gb is formed at this position, thus, a section of a distance T up to an edge portion Ga from Gb is made the upper layer side cuff surface 7b. In the upper layer side cuff surface 7b, the outside extended stock 7c in which the end portion Ga side is extended by a width S on the outside in the width direction than a side edge 4a of the absorber 4 is formed. In the elastic member disposed on the upper layer side cuff surface 7b, the inside elastic member 8 is disposed at a position distanced outward by a distance Y from the cuff portion Gb, and the outside elastic member 9 is disposed at a position distanced inward by a distance Z. A distance between the inside elastic member 8 and the outside elastic member 9 is U.

Figure 3:
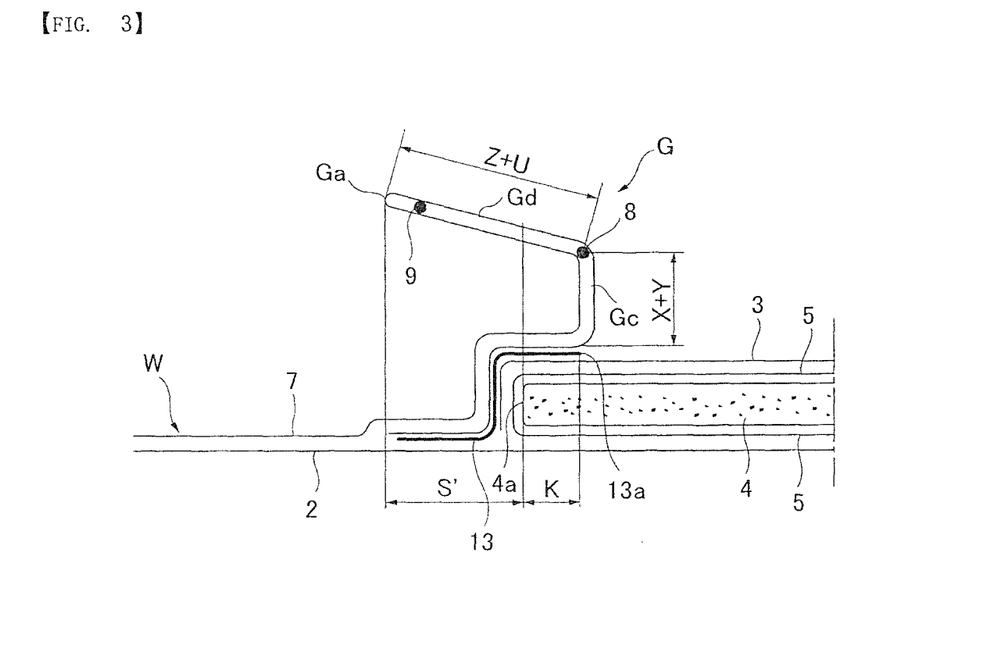
FIG. 3 is a cross-sectional view illustrating a standing-up state of the solid gather G.
Figure 4:
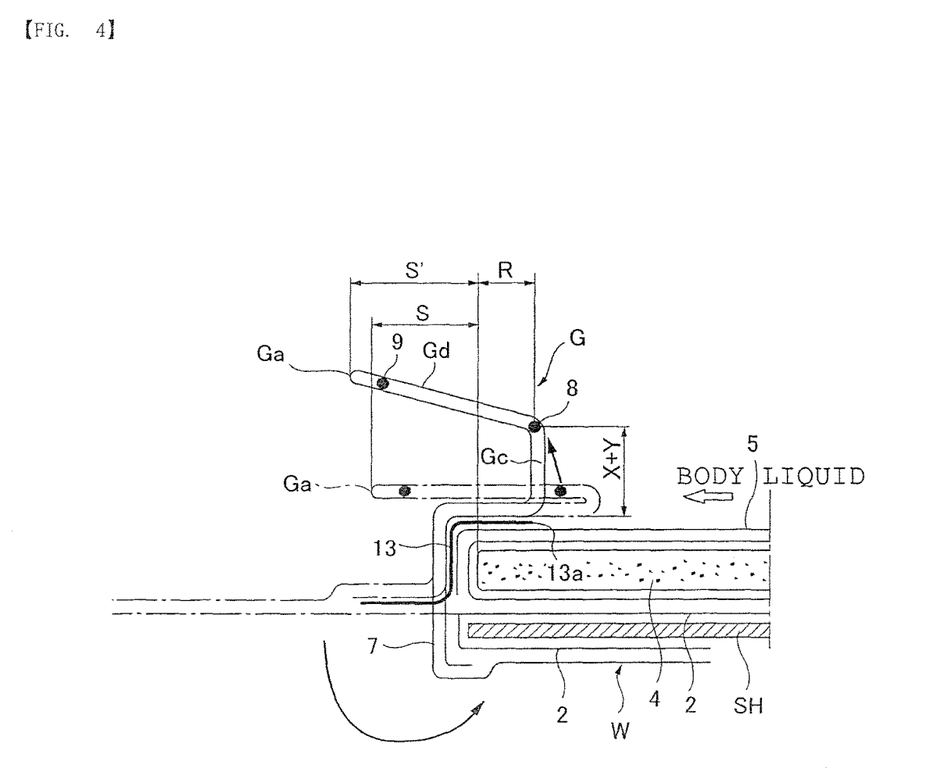
FIG. 4 is a cross-sectional view illustrating a wearing state of the sanitary towel 1.

When thus folded solid gather G, in a standing state, as illustrated in FIG. 3, stands up on the skin side with the inside edge portion 13a (outside edge portion of the non-join area 14) of the lower layer side joint area 13 as a base, a portion between from the inside elastic member 8 to the inside edge portion 13a of the lower layer side joint area 13 (section X+Y) and works as a standing wall Gc protruding from a front side of the absorber 4 (pervious front sheet 3) when the cuff portion Gb is relieved, and with the inside elastic member 8 as a bending point, an outside portion (section Z+U) of the inside elastic member 8 inclines at an inclination angle that increases toward the outward side and works as a skin-abutting surface Gd that contacts with a skin of a wearer during wearing. Then, as illustrated in FIG. 4, a portion that works as the skin-abutting surface Gd is configured to move outward in the towel width direction in the standing state relative to the folded state. That is, a distance in the width direction from a side edge 4a of the absorber 4 to an end portion Ga of the upper layer side cuff surface 7b (an amount of protrusion of the absorber from the side edge 4a) is configured such that S' of the standing state is larger than S of the folded state (S<S').

As a mechanism by which the portion that works as the skin-abutting surface Gd moves outward in the towel width direction in the standing state than in the folded state, since the inside elastic member 8 is disposed in the intermediate portion in the width direction of a portion corresponding to the non-joint area 14 of the upper layer side cuff surface 7b, that is, is disposed inward of the inside edge portion 13a of the lower layer side joint area 13, when standing-up with the inside edge portion 13a of the lower layer side joint area 13 as a base by the contractile force of the inside elastic member 8, a force that pulls the inside elastic member 8 obliquely upward in an inside edge portion 13a direction of the lower layer side joint area 13.

When wearing the sanitary towel 1 in which the gather G like this is formed on panties, as illustrated in FIG. 4, when the wing-like flap W is folded back along the side edge of substantially the absorber 4 and fixed so as to circumvolute the side edge of the panties SH, the skin-abutting surface Gd of the solid gather G moves outward in the width direction by the contractile force of the inside elastic member 8 as described above, therefore, a risk that the skin-abutting surface Gd falls down to the inside is largely reduced, and a wide surface width of the absorber 4 effective for absorbing the body liquid can be secured, and even a thin sanitary towel 1 can secure high absorptivity. Further, since the standing wall Gc protruding from a front side of the absorber 4 is formed in an inside portion in a standing state of the solid gather G, the effect of blocking the body liquid from diffusing outward can be secured and the body liquid can be blocked from laterally leaking.

Further, since the outside extended stock 7c that is extended outward of the side edge 4a of the absorber 4 is disposed on the upper layer side cuff surface 7b of the solid gather G, and the skin-abutting surface Gd is configured to move further outward in the towel width direction in the standing state than in the folded state, the case where the skin-abutting surface Gd of the solid gather G is worn in a state protruding outside of the side edge of the panties SH becomes frequent when wearing the towel, and tendency of the solid gather G falling down inward by the pressure from the inside of the root portion of the leg or the movement of the leg is largely reduced.

Still further, the solid gather G can be made thinner and the towel is more comfortable when worn because the solid gather G becomes a sheet of two-layer structure made from the lower layer side cuff surface 7a and the upper layer side cuff surface 7b in the folded state.

Figure 6:
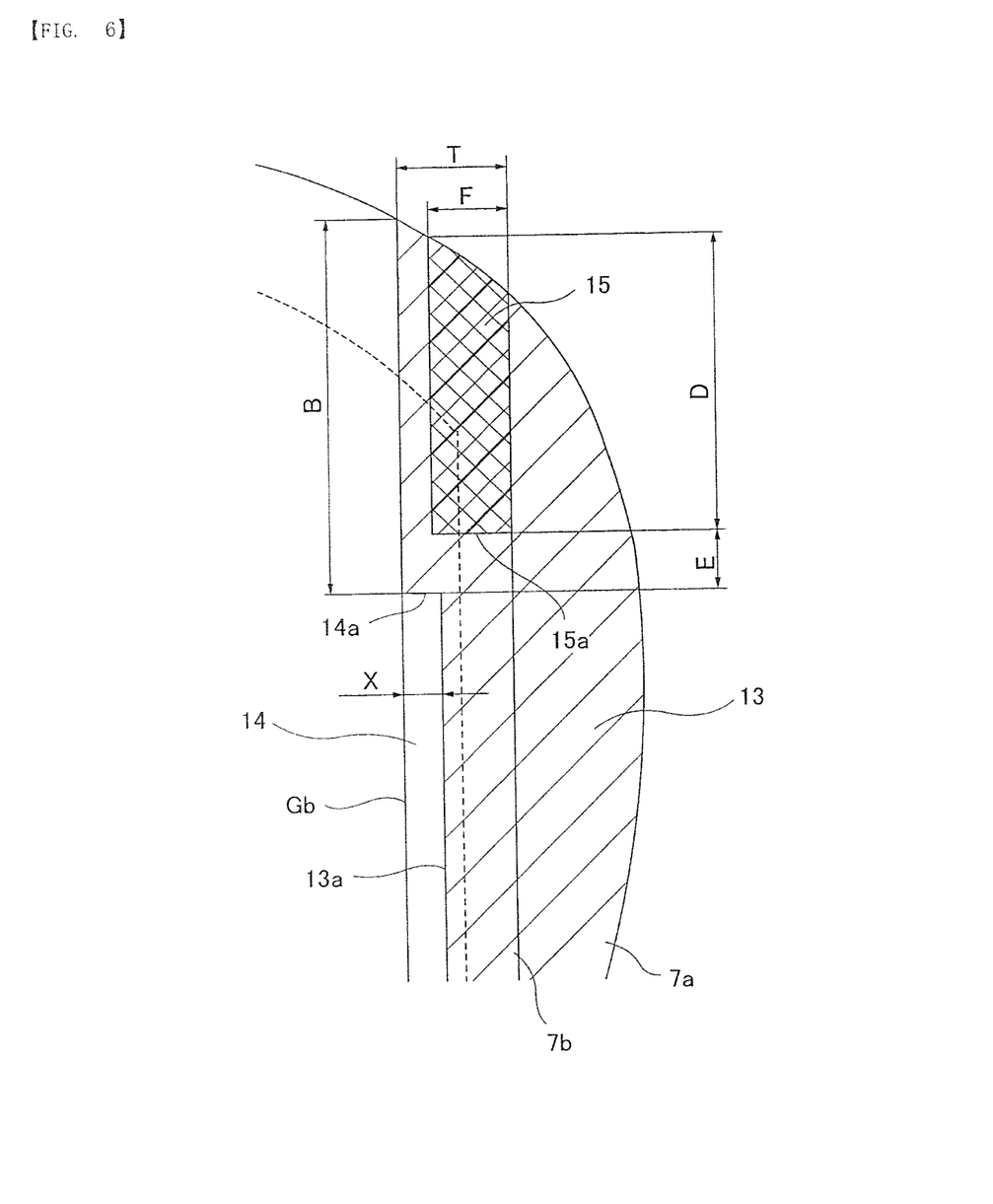
FIG. 6 is an enlarged view of a longitudinal direction end portion.

The upper layer side joint area 15 is, as illustrated in FIG. 6, with respect to the towel longitudinal direction, formed up to the end edge of the towel with a position toward the towel end portion by an interval E from the end edge of the non-joint area 14 as a base. Further, the upper layer side joint area 15 is formed with a width F narrower than a width T of the upper layer cuff surface 7b with respect to the towel width direction. Thus, when the base 15a in the towel longitudinal direction of the upper layer side joint area 15 is disposed at a position further toward the end portion than the end edge 14a of the non-joint area 14, since a tip (free end) of a portion that works as the skin-abutting surface Gd on the upper layer side tends to incline high on the skin side and the skin-abutting surface Gd tends to fit along the skin at the time of standing-up of the solid gather G, the solid gather G is blocked from falling down to the inside of the solid gather G. Further, when a width F in the towel width direction of the upper layer side joint area 15 is formed narrower than a width T, a joint area, which, if larger, could cause skin discomfort, is small, resulting in greater wearing comfort. Incidentally, the upper layer side joint area 15 is formed such that an end portion of the outside in the towel width direction locates at a tip of the upper layer side cuff surface 7b in the illustrated embodiment, but may be formed at an optional position as long as it is within the width of the upper layer side cuff surface 7b. Specific dimensions of the respective portions will be described in detail below.

As illustrated in FIG. 4, in the standing state of the solid gather G, she skin-abutting surface Gd is preferably formed such that, with the side edge 4a of the absorber 4 as a base, a width S' of a portion that extends outward is larger than a width R of a portion that intervenes at a position overlapping with the absorber 4 (S'>R). When the skin-abutting surface Gd is disposed at a position that satisfies such a relationship, the skin-abutting surface Gd can be further blocked from falling down to the inside. A ratio of S':R is preferably set at about 2:1. A method of adjusting the width R of the inner side is performed by adjusting a position of the inside edge portion 13a because the inside elastic member 8 moves substantially on the inside edge portion 13a of the lower layer side joint area 13 in the standing state.

Further, as illustrated in FIG. 3, a height (X+Y) of the standing wall Gc of the solid gather G is preferably set smaller than a width (Z+U) of the skin-abutting surface Gd. When the height (X+Y) of the standing wall Gc is too high, the risk of failing down on the inside becomes higher and, when a gap between a towel surface and the skin is small, the standing wall Gc collapses to tend to cause twists or wrinkles and to generate uncomfortable feeling when wearing. On the other hand, a contact area with the skin is preferably made as large as possible because the skin-abutting surface Gd has a portion that comes into close contact with the skin to block the leakage of the body liquid. Therefore, by defining a height of the standing wall Gc appropriate from a relationship with a width of the skin-abutting surface Gd, the solid gather G that does not cause the leakage and is excellent in the wearing feeling can be formed.

As the inside elastic member 8 and outside elastic member 9, a filamentous elastic extendable member is preferably used. Each such filamentous elastic extendable members is disposed inside of the double sheets of the side nonwoven fabric 7 in a predetermined elongated state, and both ends or appropriate positions in the longitudinal direction are fixed. A degree of extension (tension) of the filamentous elastic extendable member is preferably set to 120 to 160% (with a natural state as 100%, an extension degree from this state is 1.2 times to 1.6 times). Further, the tension of the outside elastic member 9 is preferably set to the same or more than the tension of the inside elastic member 8, specifically, is set higher by 0 to 20%. Thus, since the skin-abutting surface Gd is formed at an inclination angle in which the outside elastic member 9 is disposed is relatively higher than the inside on the skin side in the standing state of the solid gather G, the skin-abutting surface Gd tends to more easily follow the body, and the close contact with the skin can be further improved. A diameter of the filamentous elastic extendable member is preferably about 310 to 610 dtex, the diameters of inside elastic member 8 and the outside elastic member 9 may be the same or may be different. When the diameter of the outside elastic member 9 that is relatively larger than the diameter of the inside elastic member 8 is used, even when degrees of extension of the both are set to equal, the extension force (tension) of the outside elastic member 9 can be higher than the contractile force of the inside elastic member 8.

The inside elastic member 8 and outside elastic member 9 are preferably not fixed to the side nonwoven fabric 7 (in a natural state without application of the tension) in the range of about 10 mm each from the both ends thereof in the sanitary towel 1 longitudinal direction. When the elastic member is fixed at the both ends in the longitudinal direction, the both end portions of the product tend to be bent due to the contractile force of the elastic member, and the uncomfortable feeling tends to be generated during wearing.

Each of the tensions of the inside elastic member 8 and outside elastic member 9 is preferable, in the relationship with the torsional strength of the absorber 4, to be about 140% (in the case of the filamentous elastic extendable member of 470 dtex) in the case of the torsional strength of the absorber 4 being about 23 to 27 gf·cm/cm. Further, when the absorber 4 has weak stiffness such that the torsional strength is about 19 to 23 gf·cm/cm, in order to block the absorber 4 from shrinking due to contraction of the elastic member to result in degradation of the close contact with skin of the skin-abutting surface Gd of the solid gather G, each of the tensions of the elastic members 8 and 9 is preferably about 130% (in the case of the filamentous elastic extendable member of 470 dtex).

The torsional strength (gf·cm/cm) is the strength when the sample is twisted by 70 deg and the torsional strength 70 degree was measured using KES large scale torsion tester. The KES large scale torsion tester is a large-scale torsion tester manufactured by KATO TECH Corp. (KES-YN-1-B), and the size of the sample of an absorber was set to 150 mm (in length)×55 mm (in width), and the measurement was performed under the following test conditions.

Measurement chuck portion: edges of upper chuck and lower chuck are set in accordance with the edge of a sample,
Chuck interval: 115 mm,
SENS (recording sensitivity): 2, Torsion angle: 7/CONTROL: 7,
SPEED: 12 cm/s, and
Sample width: 6 cm.
Measurements were performed between torsional angles of 0 to ±70 deg, and graphs (X-axis: deg, Y-axis: gf·cm/cm (stress)) were prepared, and from the graphs, inclination of the graph between torsional angles of 10 to 65 deg, that is, the torsional strength 70 deg was read.

Figure 5:
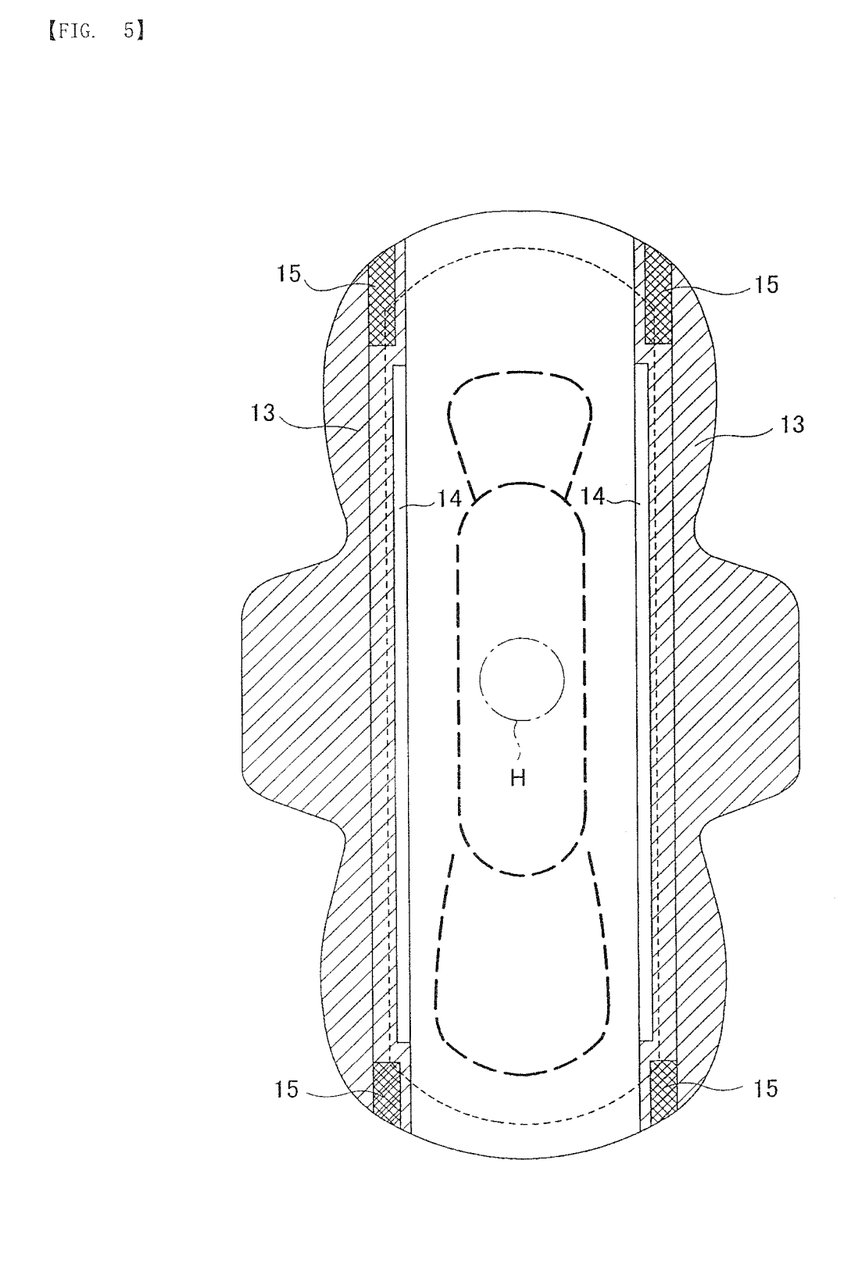
FIG. 5 is a development view illustrating a joint area or the like of a side nonwoven fabric 7.

In the longitudinal direction both ends of the sanitary towel 1, as illustrated in FIG. 5, the lower layer side cuff surface 7a of the side nonwoven fabric 7 is joined to the constituent member on the lower layer side by the lower layer side joint area 13 from the lateral side to the cuff portion Gb, and the upper layer side cuff surface 7b is joined to the lower layer side cuff surface 7a in the upper layer side joint area 15. In FIG. 5, a slash shows the joint area 15 of the lower layer side cuff surface 7a and the constituent member on the lower layer side of the side nonwoven fabric 7, and the crossing slash shows the upper layer side joint area 15 of the lower layer side cuff surface 7a and the upper layer side cuff surface 7b.

Next, as shown in FIG. 6, the detailed dimension of the solid gathers G, the dimension of the non-joint area 14, and so on will be described. The width T of the upper layer side cuff surface 7b is preferably set to 10 to 20 mm. Since a touch area with the skin will decrease if this width T is made small, the wearing comfort is assured, but when it is made too small, there is a possibility that the solid gather G cannot withstand the pressure from the inner portion of the root of a leg or a motion of the body and folds back to the inside.

As positions of the elastic members 8 and 9 disposed on the upper layer side cuff surface 7b, as shown in FIG. 2, the inside elastic member 8 is disposed at an intermediate portion in the width direction corresponding to the non-joint area 14, that is, between the inside edge portion 13a of the lower layer side joint area 13 and the cuff portion Gb, the distance Y from the cuff portion Gb is set to 5 mm or less, preferably set to 1 to 4 mm, the outside elastic member 9 is disposed in the intermediate portion in the width direction of the outside extended stock 7c portion, that is, between the side edge 4a of the absorber 4 and the end portion Ga, the distance Z from the end portion Ga is set to 5 mm or less, preferably to 1 to 4 mm. The interval U between the inside elastic member 8 and the outside elastic member 9 is desirably set to 6 to 15 mm. It is desirable to provide the distance Y described above in order to form the standing wall Gc of the solid gathers G, and the outside elastic member 9 is desirably provided with the distance Z described above rather than disposing the end portion Ga in order to alleviate the stimulus of the elastic member to the skin.

The width X of the non-joint area 14 described above is preferably set to 2 to 7 mm. The range of a towel longitudinal direction range of the non-joint area 14 is, as illustrated in FIG. 5, preferably provided including at least the longitudinal direction range of the body fluid discharge portion H up to near the upper layer side joint area 15 of the upper layer side cuff surface 7b.

The dimension of each portion of the upper layer side joint area 15 is, as illustrated in FIG. 6, preferably set such that the distance E between the end edge 14a of the non-joint area 14 and the end edge 15a of the upper layer side joint area 15 is shorter than the towel longitudinal direction length D of the upper layer side joint area 15 described above, and specifically preferably set to about 2 to 7 mm. The towel longitudinal direction length D of the upper layer side joint area 15 described above is to be set shorter than the distance B from the towel longitudinal direction end portion to the non-joint region 14, and preferably set to about 20 to 45 mm. The distance B described above is preferably about 30 to 50 mm. The width F of the upper layer side joint region 15 is preferably set smaller than the width T of the upper layer side cuff surface 7b by disposing, as illustrated in the drawing, toward the end portion Ga by remaining slight non-joint region on the cuff portion Gb side than by disposing over an entire width T of the upper layer side cuff surface 7b. The width F of the specific upper layer side joint area 15 described above is preferably set to 8 to 18 mm.

As illustrated in FIG. 2, the width S of the extended stock 7c of the upper layer side cuff surface 7b in the folded state of the solid gathers G is preferably set to about 40 to 60% of the width (Z+U) of a portion that works as the skin-abutting surface Gd at the time of standing-up. Thus, when wearing the sanitary towel 1, the skin-abutting surface Gd protrudes from the side edge of the short to be easy to wear and the close contact between the skin-abutting surface Gd and the skin can be improved.

The lower layer side joint area 13 described above is preferably formed from the side edge portion, of the sanitary towel 1 to the position which overlaps with the absorber 4, as illustrated in FIG. 2 and FIG. 5. In the example shown in FIG. 2, the graphic display line of the lower layer side joint area 13 of the side edge side portion (a wing-like flap W portion and its vicinity) of the sanitary towel 1 is omitted, but originally as illustrated in FIG. 5, it is disposed by extending to the side edge portion of the sanitary towel 1. In the longitudinal direction range in which the non-joint area 14 containing at least the body fluid discharge portion H is formed, as illustrated in FIG. 2, the absorber 4 and the lower layer side joint area 13 are disposed so as to have an overlapping stock K. Thus, in the standing state of the solid gathers G, since the standing wall Gc is always formed in the interposition position of the absorber 4 as shown in FIG. 3, the body fluid dammed up by the standing wall Gc becomes easy to be absorbed.

The invention claimed is:
1. A sanitary towel comprising an absorber disposed at least on a front side of an impervious back sheet and a solid gather formed along a longitudinal direction of each side portion of the front, skin-facing side of the sanitary towel, wherein:
  when the solid gather is folded back in a folded state to a lateral side at a folding back portion disposed at a position where a sheet extended in a center side direction from a lateral side of the sanitary towel overlaps the absorber, a lower layer joint area that has a lower layer cuff surface and an upper layer cuff surface and in which the lower layer cuff surface and another part of the sanitary towel on a layer lower than the lower layer cuff surface are joined is formed over a predetermined widthwise center area of the sanitary towel, a non-joint area is formed that extends over a predetermined length of the sanitary towel including at least a portion configured to correspond to the body liquid discharging part of a wearer of the sanitary towel and in which the lower layer cuff surface and another part of the sanitary towel are joined in the vicinity of the cuff portion, an upper layer joint area in which the upper layer cuff surface and the lower layer cuff surface are joined in both end portions in the sanitary towel longitudinal direction is formed, an outside extended stock portion in which the outside in the width direction of the upper layer cuff surface is extended outside of an end edge of the absorber is disposed on the upper layer cuff surface, an inside elastic member is disposed along the longitudinal direction in an intermediate portion in a width direction corresponding to the non-joint area of the upper layer cuff surface, and further outside in the width direction, an outside elastic member is disposed along the longitudinal direction, the upper layer joint area is formed to the end edge of the sanitary towel with a position further toward an end of the sanitary towel apart by a predetermined interval from the end edge of the non-joint area as a base relative to the sanitary towel longitudinal direction, and is formed with a narrower width than a width of the upper layer cuff surface with respect to the sanitary towel width direction, and the solid gather, by standing up on a skin side with an inside edge portion of the lower layer joint area as a base in a standing state, acts as a standing wall from which a portion from the inside elastic member to the inside edge portion of the lower layer joint area protrudes from a front of the absorber, and an outside portion of the inside elastic member acts as an abutting surface at the time of wearing, and a portion that works as the abutting surface is configured to move further to the outside in the sanitary towel width direction in the standing state than in the folded state.

2. The sanitary towel according to claim 1, wherein a thickness of the napkin excluding a central elevated portion comprising the absorber is 3 mm or less.

3. The sanitary towel according to claim 1, wherein, in the standing state of the solid gather, a skin-abutting surface is formed such that the width of the portion extending outward of the end edge of the absorber is larger than the width of a portion intervening in a position that overlaps with the absorber.

4. The sanitary towel according to claim 1, wherein the outside elastic member is disposed in an intermediate portion in the width direction of the outside extended stock portion of the upper layer cuff surface.

5. The sanitary towel according to claim 1, wherein a tension of the outside elastic member is set equal to or larger than a tension of the inside elastic member.

6. The sanitary towel according to claim 1, wherein a lower layer side joint area is formed from the lateral side of the sanitary towel up to a position that overlaps with the absorber.

* * * * *